(12) United States Patent
De Kok et al.

(10) Patent No.: US 8,781,545 B2
(45) Date of Patent: Jul. 15, 2014

(54) BODY MONITORING DEVICE, BODY DATA ACQUIRING METHOD AND METHOD OF DETERMINING THE PRESENCE, LOCATION AND/OR STAGE OF A WOUND

(75) Inventors: Margreet De Kok, Eindhoven (NL); Liesbeth Van Pieterson, Eindhoven (NL); Martinus Bernardus Van Der Mark, Eindhoven (NL)

(73) Assignee: Koninklijke Philips N.V., Eindhoven (NL)

(*) Notice: Subject to any disclaimer, the term of this patent is extended or adjusted under 35 U.S.C. 154(b) by 929 days.

(21) Appl. No.: 12/304,133

(22) PCT Filed: Jun. 8, 2007

(86) PCT No.: PCT/IB2007/052171
§ 371 (c)(1),
(2), (4) Date: Dec. 10, 2008

(87) PCT Pub. No.: WO2007/144810
PCT Pub. Date: Dec. 21, 2007

(65) Prior Publication Data
US 2009/0163819 A1    Jun. 25, 2009

(30) Foreign Application Priority Data
Jun. 12, 2006 (EP) ..................... 06115270

(51) Int. Cl.
*A61B 6/00* (2006.01)
*A61N 5/06* (2006.01)

(52) U.S. Cl.
USPC ............. 600/323; 600/473; 600/476; 604/88

(58) Field of Classification Search
USPC ............................ 600/323, 473, 476; 607/88
See application file for complete search history.

(56) References Cited

U.S. PATENT DOCUMENTS

| | | | | |
|---|---|---|---|---|
| 5,435,307 A * | 7/1995 | Friauf et al. | ................... | 600/317 |
| 5,779,631 A * | 7/1998 | Chance | ................... | 600/328 |
| 5,853,370 A * | 12/1998 | Chance et al. | ................... | 600/473 |
| 6,032,071 A * | 2/2000 | Binder | ................... | 600/476 |
| 6,397,099 B1 * | 5/2002 | Chance | ................... | 600/473 |
| 7,072,700 B2 * | 7/2006 | Yamamoto et al. | ................... | 600/310 |
| 7,860,554 B2 * | 12/2010 | Leonardi et al. | ................... | 600/473 |
| 2003/0088162 A1 * | 5/2003 | Yamamoto et al. | ................... | 600/310 |
| 2006/0173253 A1 * | 8/2006 | Ganapathy et al. | ................... | 600/310 |
| 2006/0241495 A1 * | 10/2006 | Kurtz | ................... | 600/476 |
| 2008/0312517 A1 * | 12/2008 | Genoe et al. | ................... | 600/323 |
| 2009/0204185 A1 * | 8/2009 | De Kok et al. | ................... | 607/88 |
| 2009/0318908 A1 * | 12/2009 | Van Pieterson et al. | ................... | 606/9 |

* cited by examiner

Primary Examiner — Long V. Le
Assistant Examiner — Angela M Hoffa
(74) *Attorney, Agent, or Firm* — Larry Liberchuk

(57) ABSTRACT

Body monitoring device, having a surface and configured to be applied to and/or near the body, comprising at least one light source and at least one photo detector. The at least one light source emits light in at least a direction away from the surface. The at least one photo detector is configured to detect light that is emitted by the at least one light source and reflected by the body in a direction towards said surface.

8 Claims, 6 Drawing Sheets

BODY MONITORING DEVICE, BODY DATA ACQUIRING METHOD AND METHOD OF DETERMINING THE PRESENCE, LOCATION AND/OR STAGE OF A WOUND

The invention relates to a body monitoring device.

The invention also relates to a body data acquiring method.

Furthermore the invention relates to a method of determining the presence, location and/or stage of a wound.

Light, particularly IR and/or red light, is known to have beneficial effects on the human body such as, but not limited to, effective relief of muscular pains and stiffness of the joints; removal and/or reduction of bacteria, for example in ulcers or acceleration of wound repair; stimulating the fibroblasts for collagen production, for stabilizing connective tissue and healing wounds, for example necrotic depths in burn wounds; light induced blood vessel and lymphe vessel vasodilation for possible aiding in cellulite treatment, acne and/or wrinkels; preventing and/or healing inflammation like eczema; healing of particular skin diseases; and more.

By applying light to the body, i.e., phototherapy, a stay in a hospital after an accident or surgery can be shortened and the recovery, for example at home, can be accelerated. Aesthetic/cosmetic therapy, for example possible improvement of the skin, may also profit from phototherapy. Beneficial phototherapy devices are known that are provided with LEDs (Light Emitting Diodes) for emitting light to the skin.

There are many different kinds of wounds. So-called partial-thickness wounds penetrate the outer layers of the skin (the epidermis and the superficial dermis) and heal by regeneration of epithelial tissue (skin), whereas full-thickness wounds involve a loss of dermis (deeper layers of skin and fat) and of deep tissue, as well as disruption of the blood vessels, wherein during the healing process a scar is produced.

Wounds can furthermore be classified by stage. Stage I wounds can be characterized by redness or discoloration, warmth, and swelling or hardness. Stage II wounds partially penetrate the skin. Stage III full-thickness wounds penetrate up to the tough white membrane (fascia) separating the skin and fat from the deeper tissues. Stage IV wounds may be damaging to muscle or bone and may cause affecting of adjacent tissue. Stage IV wounds also comprise post-operative wounds, i.e. wounds in the organs or tissue that have undergone the surgery.

Different measurements are taken to treat wounds. For example, in thorax-wounds, e.g. wounds that are caused by cardio surgery and/or pulmonary surgery the wound may be located relatively deep in the body. Hence it might occur that an infection occurs at a deeper level, whereas the cut for operation in the epidermis is already closed. In this case sometimes the wound is re-opened to remove the infected wound fluid and the wound is kept open and/or provided with a drain for a period of time to allow the body to drain off the wound fluid. When the infection is under control the wound may close normally again. An infection under the skin can become visible by redness of the skin, pain experienced by palpation and/or swelling of the wound. Detection of the infection in an earlier phase is difficult with known clinical practice. For example, in case of infection surrounding tissue may be well perfused, i.e. in a last phase of healing, but at the infectious spot itself, the wound fluid will not have a high blood perfusion. Necrosis may occur in tissue with low perfusion and the necrotic tissue should be removed as soon as possible, also at deeper levels. Related to the perfusion, the oxygen saturation of the blood can be a measure for the healing of the wound.

A goal of the invention is to provide means for acquiring data about healing of the wound.

Another goal of the invention is to acquire data about healing of the wound.

These and other goals of the invention can be achieved individually or in combination and are not set out in any significant or preferred order, nor are the following aspects of the invention.

In a first aspect, a body monitoring device is provided, having a surface and configured to be applied to and/or near the body, comprising at least one light source and at least one photo detector, wherein the at least one light source emits light in at least a direction away from said surface and wherein the at least one photo detector is configured to detect light that is emitted by the at least one light source and reflected by the body in a direction towards said surface.

The body monitoring device is able to monitor changes and/or (ab)normalities in the body in time, such as for example the state of a wound. By comparing the detected signals with known values, for example from medical science, and/or earlier recorded data, changes and/or abnormalities can be discovered and/or the local state of the body can be determined, or at least estimated.

In a second aspect, a body data acquiring method is provided, wherein at least one wavelength range of light is emitted at a body part at a specific depth, wherein at least a part of the light is reflected at said depth, and wherein the reflected light is detected and converted to signals.

In another aspect, a method is provided for detecting the presence, location and/or stage of a wound by emitting light to the body by means of at least one light source, wherein the emitted light is at least partly reflected by the body, detecting the reflected light from the body part using at least one photo detector.

In yet another aspect, a computer program product is provided, comprising an algorithm and configured to detect signals that are reflected by the body and compare the signals with predetermined data, wherein the algorithm is configured to convert and/or compare said signals.

In clarification of the invention, embodiments thereof will be further elucidated with reference to the drawing. In the drawing.

In this description, identical or corresponding parts have identical or corresponding reference numerals. The exemplary embodiments shown should not be construed to be limitative in any manner and serve merely as illustration.

Figure 1:
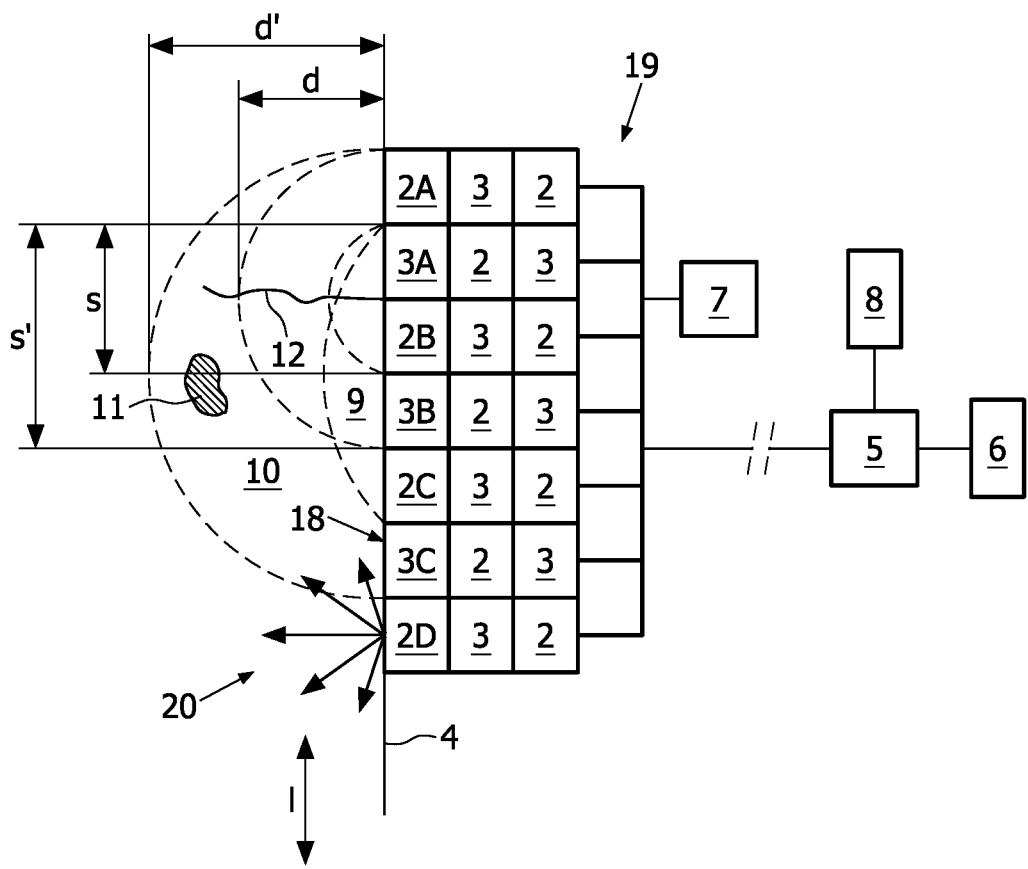
FIG. 1 shows a schematic cross section and diagram of an embodiment of a body monitoring device in use.

FIG. 1 shows an embodiment of a body monitoring device 1. A series of light sources 2A-D is connected to a power source 7 to emit light to a body part 4 from near the body part 4. In this description, there will mainly be referred to OLEDs 2 (Organic Light Emitting Diodes) as light sources 2, although other light sources 2 may be applied as well, such as for example LEDs 2, laser diodes 2, etc. Photo detectors 3A-D are provided to convert light that is reflected by the body part 4 into signals. It should be noted that light can be reflected by the skin as well as by tissue, organs, blood, vessels or other elements under said skin or exposed in for example a wound or surgical incision. A processing circuit 5 is provided to convert and compare the signals with predetermined data stored in a storage arrangement 8, where algorithms and predetermined data known in the specific medical field are applied. The processing circuit 5 may for example be connected to the OLEDs 2 and photo detectors 3 by wireless means such that the body monitoring device can be conveniently worn on the body during movement without wires attached to a computer. A user communication panel 6 may be provided to communicate the detected signals into a human readable form, for example to a specialist at a distant location. Thus a non-invasive body monitoring device 1 can be achieved.

The body monitoring device 1 can be adjusted automatically to improve the therapy. For example, the wavelength, pulse duty cycle and/or the intensity of light emitted by the OLEDs 2 can be adjusted, which will be explained in this description. Also, through the user communication panel 6 the body monitoring device 1 may be adjusted manually, for example in addition to automatic control.

Figure 2:
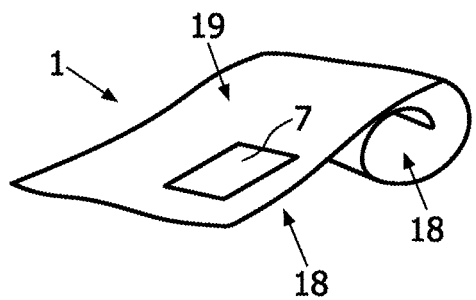
FIG. 2 shows a schematic perspective view of an embodiment of a body monitoring device.

By measuring reflected light, the state of the wounds can be estimated, for example by detecting color information of the wound. An array of light sources 2 and photodetectors 3 can be used to apply phototherapy and monitor the state of a specific body part. As shown in FIG. 2, with the aid of for example (O)LED technology, a flexible, relatively flat shaped body monitoring device 1 can be obtained that is able to conform to the curves of parts of the body of a patient. The combination of phototherapy and monitoring with (O)LED technology makes it possible to produce a self adjustable healing device 1 that is able to self adjust phototherapy settings, e.g. wavelength, triggered by monitoring results, and that is worn by the patient while maintaining freedom of movement. For example, by using (O)LED techniques a very thin shaped device 1 can be obtained, for example with a thickness of less than 7 mm, preferably less than 5 mm, for example about the thickness of a plaster, which may emit light from a nearby distance, for example less than 10 mm and most preferably between 0 and 1 mm to the body part 4. Furthermore, in an embodiment, a lithylene battery is applied as a power source 7, which can be configured relatively thin and/or flexible. Hence, in an embodiment, an intelligent healing device 1 is obtained, which can be applied substantially as easily as a plaster.

As shown in FIGS. 1 and 2, the body monitoring device has a bottom surface 18 and a top surface 19. Isotropic light 20 that is emitted by the OLEDs 2, at least in the direction of the body part 4, away from the bottom surface 18, may penetrate the inside of the body part 4, for example up to a couple of mm or even cm d, d' from the surface of the body part 4 to which the device 1 is applied, and is scattered and reflected throughout the body part 4. After penetration, some of the scattered and reflected light will return through the surface of the body part 4 and is detected by at least one of the photo detectors 3A-D. Therefore, in an embodiment, the photo detector 3 is positioned in approximately the same plane as the OLEDs 2, or in a parallel plane thereof, as can be seen from FIG. 1. This may be advantageously applied in a relatively flat embodiment of the invention. In use, an embodiment of the body monitoring device 1 may cover a body part 4, wherein a photo detector 3 detects light emitted by an OLED 2 and reflected by the body part, the photo detector 3 and OLED 2 may be positioned up to as far as halfway around said body part 4, such that reflected light is detected.

As is known in the field of light scattering, the average path that a bundle of detected light, e.g. detected photons, travels from the OLED 2 to the photo detector 3 can be described as a banana shaped profile 9, 10, or more or less a curved V-shaped profile 9, 10. In FIG. 1, the banana shaped profile 9 or 10 is indicated by two dashed lines, wherein relative to the depth away from the outer surface of the body part the distance between the dashed lines increases (hence "banana-shaped").

In an advantageous embodiment, as can be seen from FIG. 1, a first photo detector 3B measures light that is emitted by an OLED 2A, which light is reflected from depths that may be up to a first distance d from the surface to which the body monitoring device 1 is applied. Another photo detector 3C, that is relatively further away from the OLED 2A than the first photo detector 3B, measures light emitted by the OLED 2A, reflected from a depth up to a second distance d' that goes deeper than the first distance d. In principle, a larger distance s between an emitting OLED 2 and a photo detector 3 causes a larger depth d, d' from which information can be obtained. This can be derived from pre-published knowledge in the field and from the fact that with an increasing distance s the detected signal reduces exponentially. Also, with an increasing distance s more light will have left the body part through the outer surface (unless a reflective coating is applied). This contributes to the knowledge that the light that leaves the body part at an increased distance s', which light is detected by the photo detector 3, will on average have traveled from an increased depth d'. It is known, that as a rule of thumb, d=s/2. The light can penetrate the body up to the level where all light is absorbed. In some embodiments, this may for example be up to several tens of cm, for example 20 cm, for certain tissue, depending on the composition of the tissue that is penetrated by light and the emitted wavelength. At body parts where the light meets bone at an early stage, the travel path of light will be shorter. An effect of the penetration of light up to mm or cm under the surface of a body part 4 is that light may stimulate certain healing processes under said surface. For example, phototherapy and monitoring according to the invention can be applied to a post-operative wound 11 of an organ under the skin while a post-operative scar of the skin is already closed. Also, the healing and/or closing of the postoperative scar of the skin can be delayed, for example on the same time as the healing of wound 11, for additional stimulation of the wound 11 until the wound 11 has reached a certain stage in the healing process.

Figure 3:
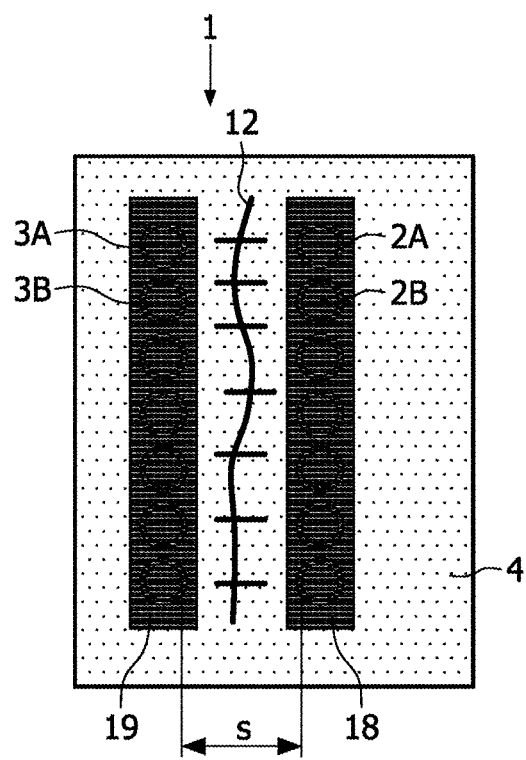
FIG. 3 shows a top view of an embodiment of a body monitoring device in use.

A basic embodiment of body monitoring device 2 is shown in a top view in FIG. 3. In this specific embodiment, LEDs 2 are located on one side of a scar 12 and photo detectors 3 are positioned on the other side of the scar 12. To adjust the depth, the distance s between a strip of LEDs 18 and photo detectors 19 can be adjusted according to the abovementioned principle.

Furthermore the traveling depth d, d' of light that is emitted to the body can be varied by adjusting the wavelength. Certain wavelengths are absorbed by certain tissue while other wavelengths may pass through or are scattered and/or reflected. By varying the wavelength the depth of light penetrating the body can be varied such that specific body parts that lie under the surface can be targeted. This is for example advantageous for treating wounds 11 (FIG. 1) that extend under the surface of the body part 4, e.g. the skin. As most wounds have other light absorption characteristics than the surrounding tissue, the detected scattered and emitted light by a photo detector 3 will vary locally.

Figure 4:
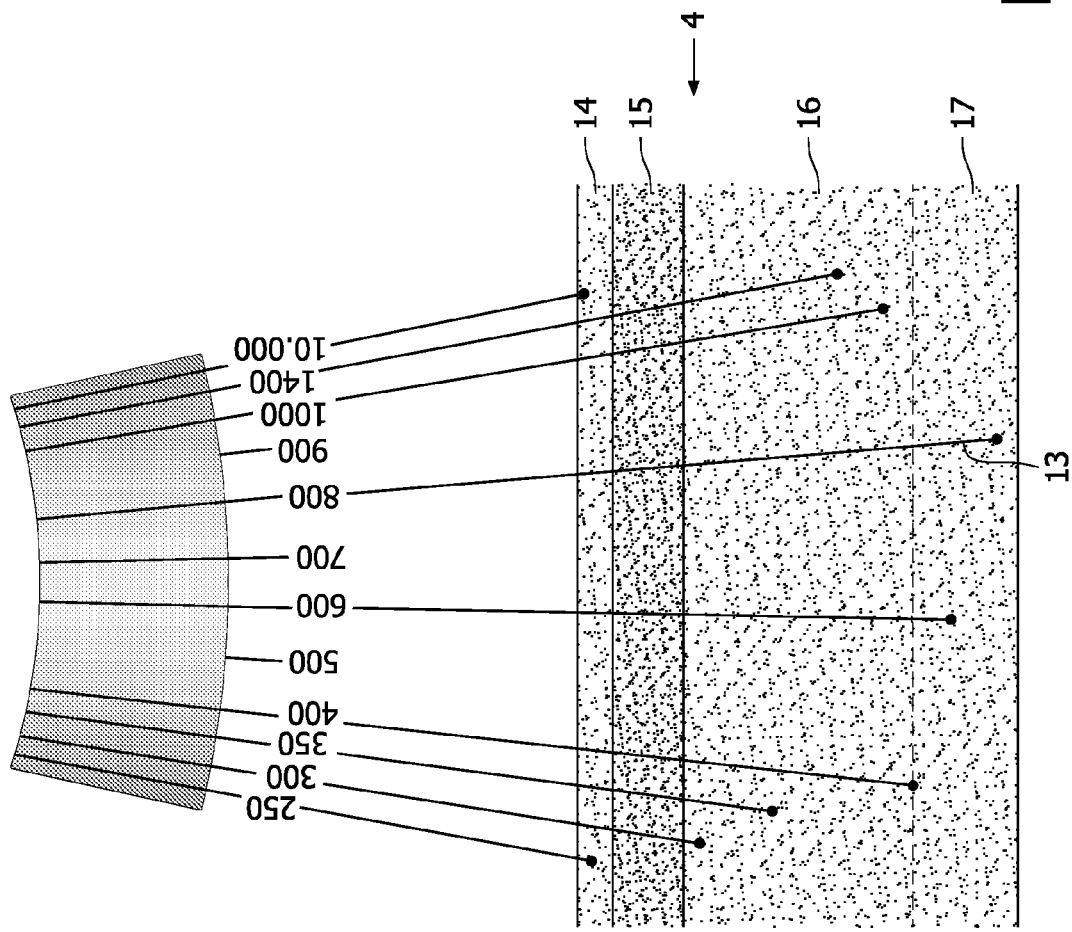
FIG. 4 shows a schematic drawing of the penetration of the skin by light.

In FIG. 4, the penetration of light at specific wavelengths into the body is indicated approximately. The numbers indicate wavelengths in nanometers and the lines to which they refer indicate travel paths of light. For example, line 13 refers to a wavelength of approximately 800 nm which penetrates relatively deep into the body, even into the subcutis layer 17. In the figure the stratum corneum layer 14, the epidermis layer 15, the dermis layer 16 and said subcutis layer 17 are indicated.

From the reflected light that has penetrated the body 4 and is converted into signals by the photo detectors 3 a certain state of a body part 4 can be determined, for example the state of an infection, or at least, a change in the state of the body part 4 by applying predetermined data and/or algorithms and by storing detected information in the storage arrangement 8 in time. This information can in turn be used to optimize the light therapy, for example adjust the area of treatment and/or adjust the wavelength to treat a specific body part at a specific depth. As the healing process changes, in time and location, the treatment can be improved and/or adjusted continuously while monitoring takes place.

As OLEDs 2 typically emit at a wavelength range of about 50-100 nm, for example between approximately 650 and 700 nm or between 400 and 500 nm. In an embodiment multiple types of OLEDs 2 with different wavelength ranges can be applied. In use, the type of OLED 2 that corresponds to the desired wavelength, i.e. the targeted depth and/or tissue, may be switched on and/or the emittance properties such as intensity and/or pulse duty cycle may be adjusted. For this, for example different OLED sheets may be stacked. Since OLEDs 2 can be configured to be transparent the configuration can be kept relatively simple. In an embodiment LEDs and/or OLEDs 2 are used as a photodiode 3 and a light source 2, such that the body monitoring device 1 can be relatively easily and cheaply manufactured. Of course OLEDS 2 with different wavelength characteristics may be positioned next to each other in an array and/or a combination of arrays and stacks of different types of OLEDs 2 can be configured.

Another way of varying/selecting wavelength ranges is by applying wavelength filters. The filters can be configured such that the selected wavelength range may be varied. Filters can also be advantageously applied to light sources 2 with large wavelength ranges, such as OLEDs 2.

In another embodiment, the wavelength is varied by adjusting the intensity of the OLEDs 2. For example, when specific phosphors are used in and/or near the light source 2, they will show a color shift when the intensity of the light source 2 is adjusted. By adjusting the intensity of light that is emitted by the light source 2 the color of the phosphors may shift. To compensate for a change of light intensity, the dose of emitted light in a certain time interval can be corrected, for example by applying and varying a pulse duty cycle, for example by means of pulse width modulation, as shown in the diagram of FIGS. 5A-D.

Figure 5A:
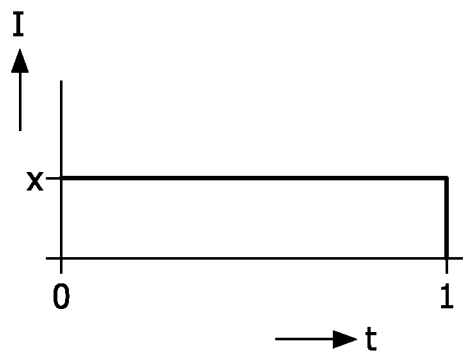
FIGS. 5A-5D show diagrams that plot light intensity against time.
Figure 5B:
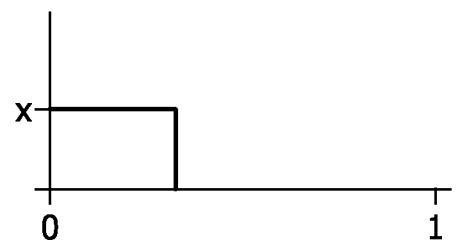
Figure 5C:
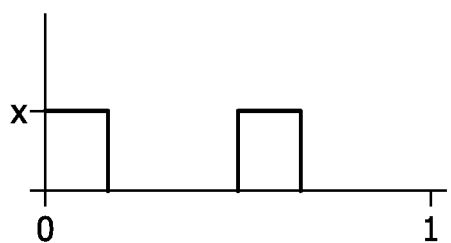
Figure 5D:
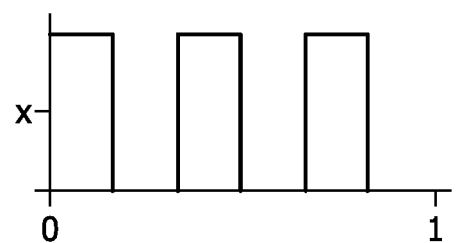

FIGS. 5A-D show diagrams wherein a vertical axis represents the intensity of emitted light I and the horizontal axis represents time t. In FIG. 5A an intensity of x is emitted without interference during a time interval of 1 time unit, a duty cycle of 100% is applied, with a peak height of x and a repetition rate of 1, providing for a total dose of x, wherein the dose equals the peak height multiplied by the duty cycle. In FIG. 5B the intensity of x drops to 0 after 33% of the time interval of 1 time unit. In this case a duty cycle of 33% is applied, with a peak height of x and a repetition rate of 1, providing for a dose of 0.33x. According to the same principle, FIG. 5C shows a duty cycle of 33%, a peak height of x, a repetition rate of 2 and a dose of 0.33x, and FIG. 5D shows a duty cycle of 50%, a peak height of 2x, a repetition rate of 3 and a dose of x. Of course different pulse widths may be applied, for example the light may be turned off for longer intervals and off for shorter intervals. The total dose of light is determined by the pulse width, pulse peak intensity and pulse duty cycle and the total time of the illumination sequence. This shows that at different intensities, the dose can be kept equal or may be adjusted as desired. Of course all abovementioned parameters such as duty cycle, pulse width, peak height, total time of illumination and repetition rate can be adjusted. In principle, the dose is equal to the light flux over a surface multiplied by the emission time.

The intensity and flux limit for monitoring are given by what is called the maximum permissible exposure (MPE), for which known tables exist. For example, when emitting light to the skin for intervals longer than 10 minutes, the threshold is approximately 0.2 $W/cm^2$. In case of therapeutic light administration the possible presence of an intensity threshold with any given light dose can be taken into account. Also MPE tables are known which indicate maximum exposure amounts at specific wavelength ranges. These tables can be incorporated in the predetermined data for safety.

In an embodiment light sources 2 are used, particularly inorganic LED types 2, that show a color shift when changing a forward current, for example from green to red and/or vice versa. With these light sources, if the forward current is increased, the color spectrum shifts to shorter wavelengths. Here, again, the dose amount can be corrected by varying the duty cycle characteristics, for example as shown in FIGS. 5A-D.

In another embodiment, the wavelength of LEDs 2 is adjusted by adjusting the temperature of the LED 2, for example by heating the LED 2. In this case, the LED 2 will show a shift in the emission spectrum. Again, a loss of intensity can be compensated for by correcting the dose.

Abovementioned embodiments for varying the wavelengths serve as examples. More ways of adjusting the wavelength exist. Mentioned and other ways for wavelength adjustment can be combined to achieve optimal wavelength adjustment. For example, multiple stacked layers of LEDs 2 may be applied, whereas filters are used for wavelength range selection and the forward current may be changed. With the aid of at least one of these techniques, the wavelength range can be fine-tuned, i.e. adjusted gradually, to a desired wavelength range, between a lowest and highest value that are defined by the configuration of the light sources 2. A lowest value might for example be approximately 250 nm and a highest value for example approximately 1000 nm, although lower and higher values can also be advantageous, for example for measuring moist and/or temperature, in the case of higher values. For safety, for example MPE tables can be referred to. By fine-tuning, emission and/or reflection can take place at a desired depth relatively accurately.

In addition to or apart from the varying of wavelengths, different depths can be reached by the light, because of the natural differences in light absorption of certain body parts. For example more blood rich regions will absorb more light and hence will let less light pass through and/or be scattered and/or reflected.

In an embodiment, agents are applied to the body. An agent can be photo-activated such that it will treat the body part when light reaches the agent. Here, the agent functions as a type of medicament that needs to be photo-activated, for example for disinfecting a wound. Also, agents can be applied that change the light absorption properties of specific body parts and/or enhance light resolution, wherein agents are used to increase the possibility that light reaches a desired depth, or at least a desired location. This may for example be advantageous in the case of infections.

A known example of a type of agent is a targeting agent. This type of agent is aimed at a particular kind of tissue and/or other body element, like for example a protein that is present in a tissue that is targeted for treatment.

Another known example of a type of agent is a contrast agent, which may be brought into the body, for example by means of a catheter, infusions or injections for example into the blood vessels.

Agents may be used for monitoring and/or phototherapy. As a monitoring aid, an example of a contrast agent is omocyanine, which is a dye. At concentration levels of approximately 0.1 mg/kg body mass this agent can enhance resolution. Omocyanine is applied, for example, to the blood and absorbs light in the red part of the spectrum which brings omocyanine in an optically excited state. It emits light at around 780 nm by means of fluorescence, which can be detected advantageously by filtering out said red light used for excitation. The fluorescent light which is only emitted from the position of where the dye is present is left for detection by the photo detectors 3.

As a phototherapy aid, for example dyes acting as an agent, can be used, wherein the dye is e.g. physically and/or chemically altered and/or activated by the light that is administered through the body, e.g. the skin. The dye can be designed to be a functional medicine that performs its healing task when it is altered and/or activated by the light, for example in the blood vessels, in the interstitial fluid between cells or within cells.

The state of wounds can be estimated by estimating the oxygen saturation in the blood (the amount of haemoglobin and/or oxyhaemoglobin). For this, pulse oximetry can be used. Pulse oximetry is an accepted method of monitoring the oxygen saturation. A pulse oximeter is a non-invasive device that can indicate, or at least estimate, the pulse activity of the heart and the oxygen saturation ($SpO_2$) of arterial blood. Known devices such as $SpO_2$-meters measure the amount of oxygen and/or the pulse and are applied to well-perfused body parts where it is easy to position a light source on one side of the body part and a photo detector on the opposite side. Here, red light is transmitted through well-perfused body parts like a finger, toe, earlobe, etc. and is detected by the photo detector on the other side. As opposed to these $SpO_2$-meters, with a body monitoring device 1 according to the invention it is also possible to estimate oxygen saturation, or more specifically, the state of a wound, infection and/or other condition by detecting reflected light that is reflected and scattered by the body part, as can be seen from FIG. 1 by the light path 9, 10, whereas with $SpO_2$-meters, the light has to pass through the body part. The body monitoring device 1 is not confined to detecting the state of relatively thin and well perfused specific body parts such as earlobes or fingers, but can measure, or at least estimate, certain conditions throughout a relatively large part of the body. Although absolute measures of blood volume and blood oxygenation may be difficult to obtain in deeper lying tissues, a change in their values can be measured and hence the progress or decline of healing of the wound can be monitored.

Figure 6:
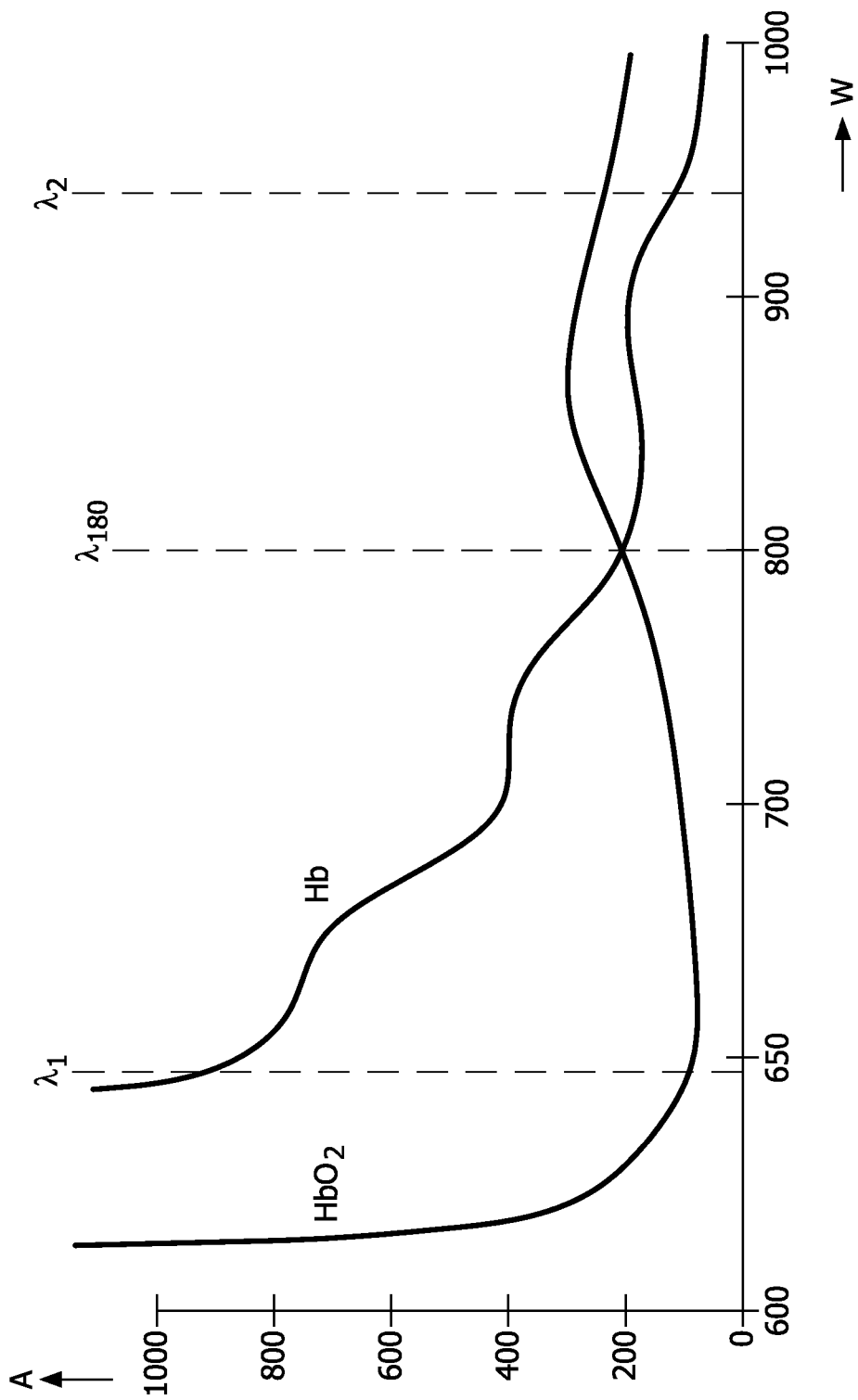
FIG. 6 shows a diagram that plots absorption of light (extinction coefficient) against wavelength.

FIG. 6, known in the medical field, shows a vertical axis A that is a measure of the absorption of light (extinction coefficient) that is plotted against a horizontal axis W that represents a measure of the wavelength. The curves $HbO_2$ and Hb represent the absorption of oxyhaemoglobin ($HbO_2$) and haemoglobin (Hb) respectively, at particular wavelengths. $HbO_2$ and Hb show different absorption as a function of wavelength, except at an isobestic wavelength ($\lambda_{ISO}$), indicated by $\lambda_{ISO}$. At $\lambda_{ISO}$, the total volume of blood that is pumped through the body can best be measured, which may be a wavelength of approximately 800 nm. At a wavelength of for example 660 nm ($\lambda_1$) blood with low oxygen saturation (Hb or reduced Hb) will show more absorption. At higher wavelengths, beyond the isobestic wavelength, such as approximately 940 nm ($\lambda_2$), blood with higher oxygen saturation ($HbO_2$) will absorb more light. At the isobestic wavelength, the amount of light absorption of haemoglobin and oxyhaemoglobin is equal. Since wounds and/or inflammations generally show less oxygen saturation than surrounding tissue, this provides for a method to detect certain tissue conditions, such as for example wounds and/or inflammations, at an early stage. For example 'redness' of the skin, 'darkness' of the blood, etc. are indicators for infections and/or inflammations. With the body monitoring device 1, for example, infections and/or inflammations that are under the skin, can be detected at an early stage. Also their change over time can be monitored.

Of course it has to be taken into account that different body parts may show different levels of blood perfusion and/or other light absorption characteristics. For example, for tissues with a higher density the scattering at shorter wavelengths may give rise to more attenuation of light and hence the optimum wavelength to determine the oxygenation of the blood may shift to longer wavelengths. Therefore, for example the wavelength range, agent and/or distance d of the body monitoring device 1 can be adjusted such that the targeted tissue is stimulated by the light.

With the aid of the body monitoring device 1, for example the presence of pus, bone, blood cloths, necrotic tissue and/or fatty tissue can be detected, which all can be indicators for the progress or lack of progress of a healing process. By using multiple wavelength ranges, discrimination of tissue is possible.

In an embodiment, the body monitoring device 1 monitors continuously over time and compares its findings with predetermined data that are known from the field or that have been recorded at an earlier stage in the monitoring process. Comparisons can be made with absolute values and/or with values that are found during the monitoring process. In this way different states and/or changes in the wound can be found and for example, a phototherapy process can be adjusted automatically. Also, the body monitoring device might for example be connected to the user communication panel 6 and/or audio and/or visual communication means for providing a warning signal or any kind of signal to inform a person about the state of the monitored location. Then, phototherapy settings can be adjusted automatically or manually. For example light can be targeted at a different depth by administering and/or adjusting an agent manually and/or automatically. In some cases, medical intervention, even surgery, might follow to treat the detected infection or necrosis.

In particular embodiments, the body monitoring device 1 is provided with mechanisms for administering medicaments, a temperature regulating mechanism, electro stimulation and/or mechanical vibration, for example for (delicate) massage purposes or the reduction of pain or itch.

Furthermore, by varying the parameters such as pulse duty cycle, peak height of intensity, dose and/or repetition rate as shown in FIGS. 5A-D the therapy can be adjusted to be more optimal. By monitoring the effect of the light on the wound, (at least one of) these parameters can be adjusted to achieve better therapy. For example, by varying these parameters in time a dynamic phototherapy may be applied such that particular body elements are stimulated in a dynamic way, thereby enhancing the healing process.

In this description, OLEDs 2 are used to illustrate an advantageous embodiment of the invention. Of course the invention should not be limited to the use of OLEDs 2 as light sources 2. Instead, LEDs 2 can be advantageously used as well. Also, other light source techniques can be applied, for example, lasers, laser diode techniques, halogen lamps, etc. The light source 2 can for example be directed to a desired body part by fibers or other light guides, for example in combination with coupling elements to direct the light to a desired location. Specific light sources 2 can be chosen according to the desired accuracy, precision, temperature characteristics, life span, intensity and/or wavelength range characteristics, and more. Light sources 2 may for example emit from a further distance from the body part, not necessarily against or near the body part. Also a combination of different types of light sources 2 can be advantageous. Furthermore, reflective coatings may be applied, for example for reflecting light that is reflected by the body, such that higher fluxes may be obtained.

Examples of photo detectors 3 may include but are not limited to (O)LEDs, photodiodes, laser diodes, lasers, and other photo detectors that are known in the field. Next to photo detectors, additional detectors 3 such as for example temperature sensors, scent sensors, gas sensors and/or color sensors can be applied.

Figure 7:
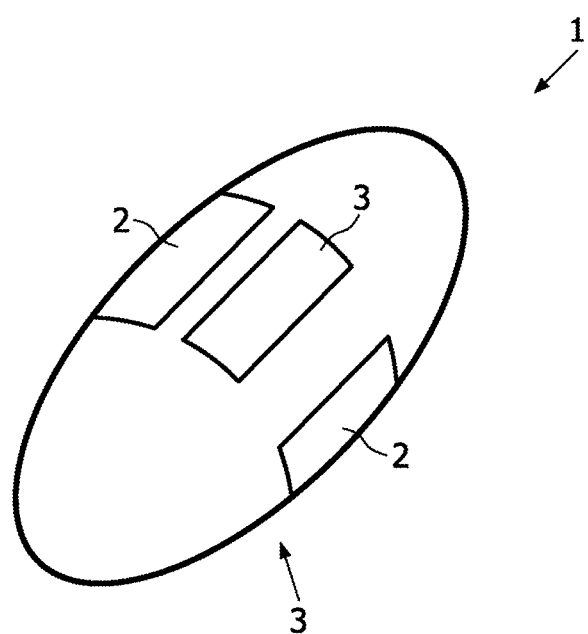
FIG. 7 shows a drawing of another embodiment of a body monitoring device.

In an embodiment, a body monitoring device 1 is configured to be located inside the body, for example to monitor internal organs. An illustrative example of such an embodiment is illustrated in FIG. 7. This should also be understood as applied to the body. For this, a body monitoring device 1 according to the invention may for example be adjusted to a suitable size and form. Furthermore, with the use of OLEDs 2 and/or specific photo detectors 3, a body monitoring device 1 in the form of a sheet can be configured to be torn and/or cut such that it can be divided into multiple body monitoring devices 1 of different sizes.

The invention is not limited to wound monitoring, but can be applied to body monitoring in general, from which multiple treatments can profit, for example such as mentioned in the preamble. Monitoring may for example also involve monitoring the sinus tracts (red streaks indicating infected lymph vessels), swellings, (encapsulated) lesions, etc. 'Wounds' are not to be considered to be limiting in any way. The invention can be used for measuring any condition of the body that needs to be treated and allows itself to be monitored by light detection, some of which are mentioned in the preamble of this description.

It will be obvious that the invention is not limited in any way to the embodiments that are represented in the description and the drawings. Many variations and combinations are possible within the framework of the invention as outlined by the claims. Combinations of one or more aspects of the embodiments or combinations of different embodiments are possible within the framework of the invention. All comparable variations are understood to fall within the framework of the invention as outlined by the claims.

The invention claimed is:

1. A body monitoring device, having a surface and configured to be applied to and/or near the body, comprising:
at least one light source; and
at least one photo detector, wherein the at least one light source emits light in at least a direction away from said surface and wherein the at least one photo detector is configured to detect light that is emitted by the at least one light source and reflected by the body in a direction towards said surface, wherein the body monitoring device is at least partly flexible for substantially extending along the curves of the body, wherein the body monitoring device has a lateral direction parallel to said surface and has a thickness perpendicular to said lateral direction, wherein the thickness is less than approximately 7 millimeters, and wherein the body monitoring device is further configured to apply dynamic phototherapy, said body monitoring device further including a control system configured to process the detected light into oxygen saturation values, wherein said control system is responsive to the oxygen saturation values for dynamically adjusting the light emitted from the at least one light source for monitoring a specific portion of the body and said control system is responsive to the oxygen saturation values for dynamically adjusting the light emitted from the at least one light source for optimizing phototherapy applied to said specific portion of the body.

2. The body monitoring device according to claim 1, wherein the at least one light source is configured to emit light at multiple wavelength ranges.

3. The body monitoring device according to claim 1, wherein the at least one photo detector is configured to detect light of multiple wavelength ranges that correspond to multiple depths and/or parts of the body.

4. The body monitoring device according to claim 1, wherein the at least one light source is configured to be tuned to emit the light within a wavelength range defined between a lowest value and a highest value.

5. The body monitoring device according to claim 1, wherein the at least one photo detector is positioned in the same plane as the at least one light source and/or in a parallel plane thereof.

6. The body monitoring device according to claim 1, wherein the at least one light source comprises a LED (light emitting diode) and/or OLED (organic light emitting diode).

7. The body monitoring device according to claim 1, wherein the thickness is less than approximately 5 mm.

8. The body monitoring device as defined in claim 1, wherein said control system dynamically adjusts at least the wavelength of the light for performing monitoring, and wherein said control system dynamically adjusts at least one characteristic of the light for performing phototherapy, said at least one characteristic selected from the group including wavelength, intensity, pulse width, pulse peak intensity, pulse duty cycle, pulse peak height, pulse repetition rate, and total time of illumination.

* * * * *